United States Patent [19]

Timko

[11] 4,211,701

[45] Jul. 8, 1980

[54] SPIRONOLACTONE PROCESS

[75] Inventor: Joseph M. Timko, Kalamazoo, Mich.

[73] Assignee: The Upjohn Company, Kalamazoo, Mich.

[21] Appl. No.: 29,553

[22] Filed: Apr. 13, 1979

[51] Int. Cl.$^2$ .............................................. C07J 21/00
[52] U.S. Cl. ...................... 260/239.57; 260/239.55 C; 260/397.1; 260/397.4
[58] Field of Search .................................... 260/239.57

[56] References Cited

U.S. PATENT DOCUMENTS

| | | | |
|---|---|---|---|
| 3,194,803 | 7/1965 | Colton | 260/239.57 |
| 3,452,008 | 6/1969 | Buzby, Jr. et al. | 260/239.57 |
| 3,773,758 | 11/1973 | Weier | 260/239.57 |

*Primary Examiner*—Elbert L. Roberts
*Attorney, Agent, or Firm*—Bruce Stein

[57] ABSTRACT

Spironolactone (VIII) is produced from ethisterone (I) by formation of the lactone (IV), a halo lactone (VI) and a Δ4,6-lactone (VII).

40 Claims, No Drawings

SPIRONOLACTONE PROCESS

BACKGROUND OF THE INVENTION

7β-Acetylthio-17β-(2-carboxyethyl)-17β-hydroxyandrost-4-en-3-one lactone (spironolactone) is a diuretic marketed both alone and with another diuretic (hydrochlorothiazide). See the Physicians Desk Reference 1978, pages 1537 and 1535, respectively.

A number of methods for preparing spironolactone (VIII) are known, see for example, U.S. Pat. Nos. 3,013,012, 3,413,288, 3,682,894, 3,847,906, 3,883,512, 3,894,006, 3,897,417, 3,900,467, 3,966,714, and 4,057,543. Besides the numerous patents which disclose processes for producing spironolactone (VIII) many other patents disclosed intermediates and processes for producing intermediates which have been reported as useful in various synthetic pathways leading to spironolactone.

U.S. Pat. No. 4,057,542 in Example 3 discloses a process for transforming ethisterone (I) to its hydroxy glycol (II).

The acid glycol (III) is novel. U.S. Pat. No. 2,705,712 (Example 1A) and U.S. Pat. No. 4,057,542 (Claim 11) disclose the corresponding glycol methyl ester compounds. U.S. Pat. No. 3,506,652 in Examples 1, 3 and 5 disclose other 17β-hydroxyandrostenedione type compounds with 3-carbon side chains in the 17α-position which upon the appropriate reaction can be cyclized to form a lactone. Two process are known for adding a third carbon atom to the steroidal propargyl alcohol. U.S. Pat. No. 4,057,542 in Example 4 discloses the transformation of a 17α-ethinyl-17β-hydroxy steroid to the corresponding 17α-(2-carboxyethinyl)-17β-hydroxy methyl ester. However, this process is much different than the process utilized in the present invention. The process in U.S. Pat. No. 4,057,542, Example 4 first blocks the 17β-hydroxy group, forms the 21-carboxylate methyl ester, and then removes the 17β-hydroxy blocking group. The process of the present invention does not necessitate the blocking of the 17β-hydroxy group but permits carboxylation of the 17α-ethinyl group directly. J. A. Cella et al. in J. Am. Chem. Soc. 79, 4808 (1957) describe reacting a 17α-ethinyl-17β-hydroxy steroid [the 3β-hydroxy analog of the hydroxy glycol (II)] with ethyl magnesium bromide and carbon dioxide to give the 3β-hydroxy analog of the acid glycol (III).

The lactone (IV) is known, see U.S. Pat. No. 2,705,712 (claim 5). U.S. Pat. No. 4,057,542 (Example 5) discloses transformation of a 17α-(2-carboxyethinyl)-17β-hydroxy steroid to its corresponding lactone by reduction of the acetylenic group by hydrogenation, lactonization and acid hydrolysis of the ketal at the C-3 position. That process is similar to one step of the process of the present invention.

The ester (V) is novel. U.S. Pat. No. 3,107,241 (Example 2) discloses 3β-acetoxy-17α-(2-carboxyethyl)-17β-hydroxyandrost-4,6-diene lactone. In the ester (V) the saturation is 3,5- not 4,6-. U.S. Pat. No. 3,194,803 discloses 3-alkoxy-17α-(2-carboxyethyl)-17β-hydroxyandrost-3,5-diene lactones. The compounds of formula (V) of the present invention are esters, not ethers. U.S. Pat. Nos. 3,159,622 (Example 1), 3,452,008 (Example 1), 4,069,219, 3,194,803 (Example 1), 3,107,241 (Example 2) disclose various processes for transformation of 3-keto steroids to the corresponding 3β-acetoxy steroid.

The halo lactone (VI) is known where $R_6$ is bromine, see U.S. Pat. No. 2,946,787. U.S. Pat. No. 2,946,787 (Example 5) discloses a process for the transformation of the lactone (IV) to the 6-bromolactone (VI). The process of U.S. Pat. No. 2,946,787 transforms the lactone (IV) directly to the halo lactone (VI) while the process of the present invention protects the 3-keto group as the acylate and therefore obtains a higher yield of halo lactone (VI).

The Δ4,6-lactone (VII) is known, see U.S. Pat. No. 2,900,383. Even though U.S. Pat. No. 2,900,383 discloses the Δ4,6-lactone (VII) it does not disclose any process similar to the process used in the present invention for transformation of the halo lactone (VI) to the Δ4,6-lactone (VII).

U.S. Pat. No. 3,013,012 (Example 3) discloses a process for the transformation of the Δ4,6-lactone (VII) to spironolactone (VIII).

A number of patents disclosed processes for preparing spironolactone (VIII), intermediates, or processes for producing intermediates useful in the various synthetic pathways to spironolactone (VIII). Even though the hydroxyglycol (II), the lactone (IV), the 6-bromolactone (VI) and the Δ4,6 lactone (VII) are known, no patent alone or in combination teaches the very short and efficient processes of the present invention.

BRIEF DESCRIPTION OF THE INVENTION

Disclosed is a process for producing spironolactone (VIII) which comprises (1) reacting ethisterone (I) with a glycol of the formula:

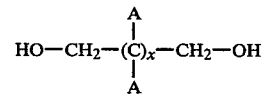

to give the hydroxy glycol (II)

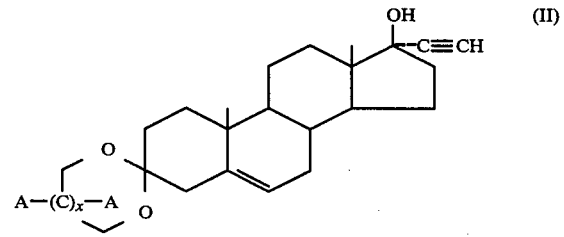

(2) carboxylating the hydroxy glycol (II) by reaction with carbon dioxide in the presence of R-Metal to give the acid glycol (III)

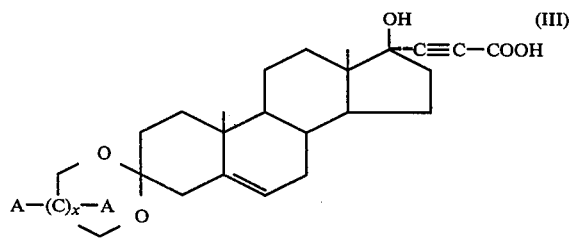

(3) reducing and cyclizing the acid glycol (III) by hydrogenation in the presence of a hydrogenating catalyst followed by acidification to give the lactone (IV)

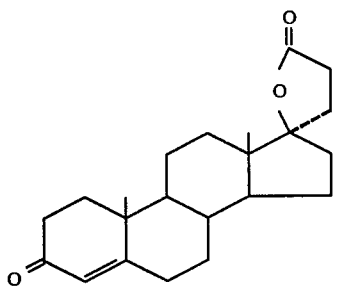

(4) esterifying the lactone (IV) by reaction with an esterifying agent selected from the group consisting of an anhydride of the formula $(R_3-CO)_2O$ or a compound of the formula $CH_3-C(CH_2)-OCOR_3$ to give the ester (V)

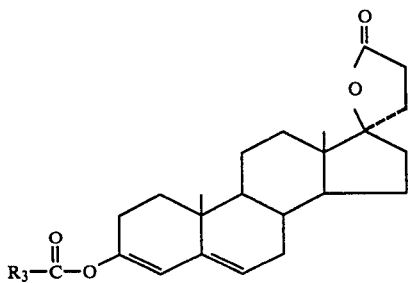

(5) halogenating the ester (V) by reaction with a halogenating agent to give the halo lactone (VI)

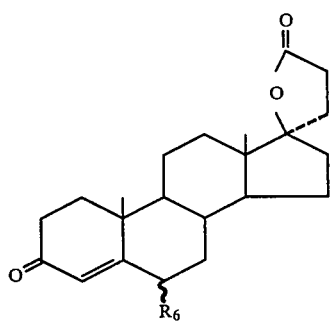

(6) heating the halo lactone (VI) in the temperature range of 20°–150° in the presence of a base to give the Δ4,6-lactone (VII)

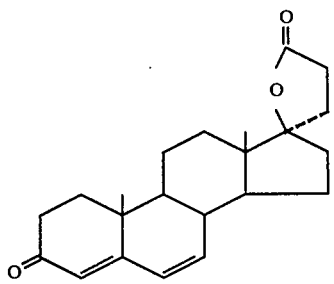

and (7) thiolacetylating with thiol acetic acid to give spironolactone (VIII).

Further disclosed is a process for producing 17α-(2-carboxyethyl)-17β-hydroxyandrost-4-en-3-one lactone (IV) which comprises (1) reacting ethisterone (I) with a glycol of the formula:

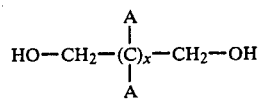

to give the hydroxy glycol (II)

(2) carboxylating the hydroxy glycol (II) by reaction with carbon dioxide in the presence of R-Metal to give the acid glycol (III) and (3) reducing and cyclizing the acid glycol (III) by hydrogenation in the presence of a hydrogenating catalyst followed by acidification to give the lactone (IV).

Also disclosed is a process for producing 17α-(2-carboxyethyl-17β-hydroxyandrosta-4,6-dien-3-one (VII) which comprises (1) esterifying the lactone (IV) by reaction with an esterifying agent selected from the group consisting of an anhydride of the formula $(R_3-CO)_2O$ or a compound of the formula $CH_3-C(CH_2)-OCOR_3$ to give the ester (V)

(2) halogenating the ester (V) by reaction with a halogenating agent to give the halo lactone (VI) and (3) heating the halo lactone (VI) in the temperature range of 20°–150° in the presence of a base to give the Δ4,6-lactone (VII).

Also disclosed is the ester (V).

DETAILED DESCRIPTION OF THE INVENTION

The present invention includes a process to produce spironolactone (VIII) from ethisterone (I). This process is set forth in Charts A and B.

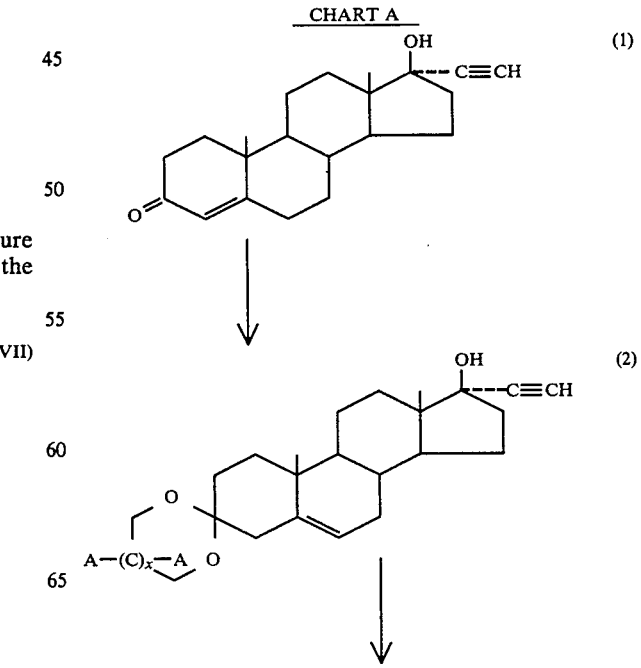

CHART A -continued

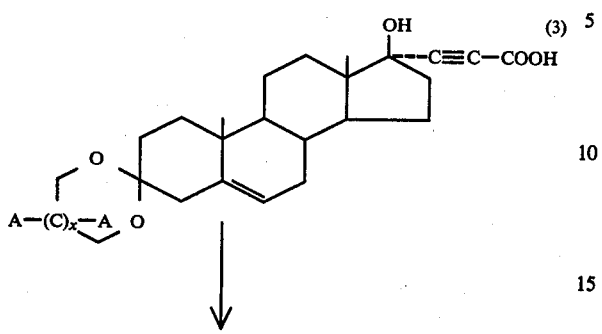

(3)

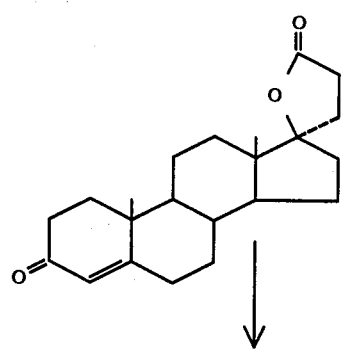

(4)

CHART B

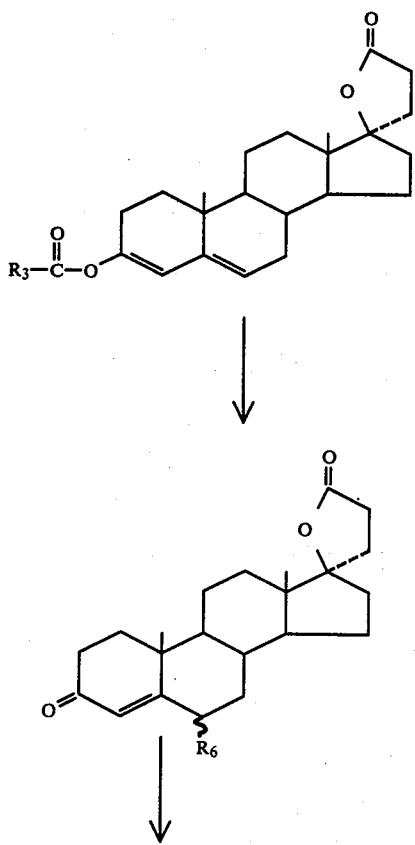

(5)

(6)

CHART B -continued

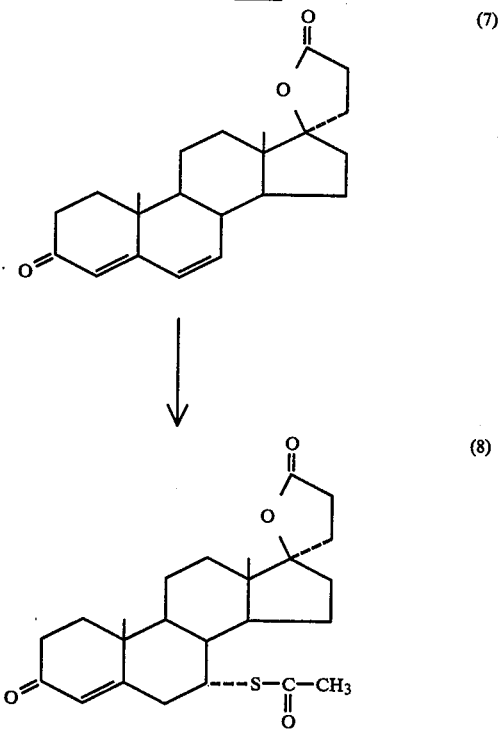

(7)

(8)

Ethisterone (I) is first transformed to the corresponding 3,3-ketal in order to protect the Δ4-3-keto system. Ethisterone is reacted with a glycol of the formula:

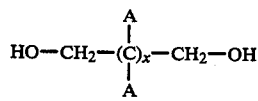

where A is a hydrogen atom or methyl group and x is 0 or 1, therefore the glycols included are ethylene glycol, propylene glycol and 2,2-dimethylpropylene glycol. The protection of a Δ4-3-keto steroid as the corresponding 3,3-ketal is a very well known reaction, see Steroid Reactions, Edited by C. Djerassi, Holden-Day, (1963), pages 2–20 and Steroids, Fieser and Fieser, Reinhold (1959) pages 307–310. The hydroxy ketal (II) is carboxylated by reaction with carbon dioxide in the presence of base at a low temperature. Solvents such as THF, dioxane or diethyl ether are suitable. It is preferred that the base be R-Metal, where R is alkyl of 1 thru 5 carbon atoms, phenyl or triphenylmethyl and where Metal is lithium, sodium, or potassium. It is preferred that R be n-butyl or phenyl. It is more preferred that R is n-butyl. It is preferred that Metal is lithium. Bases other than R-Metal may be utilized, such as potassium tertiary butoxide or a Grignard reagent but substantially lower yields are obtained when bases other than R-Metal are utilized. The reaction may be performed in the temperature range of −50° to 50°. It is preferred that the reaction be performed in the temperature range of −30° to 0°. It is preferred and more convenient to continue the reaction without isolation of the acid glycol (III).

The unsaturation in the 17α-side chain is removed by hydrogenation in the presence of a hydrogenating catalyst by the usual methods. It is preferred that the hydrogenating catalyst be selected from the group consisting of palladium on carbon, platinum on carbon, platinum dioxide, palladium on barium carbonate or palladium on calcium carbonate. It is more preferred that the hydrogenating catalyst be palladium on carbon. This hydrogenation procedure in the presence of a hydrogenating catalyst takes place preferably in the presence of a base such as triethylamine. However, other bases such as pyridine, quinoline, potassium and sodium hydroxide can be used as catalyst poisons. Solvents such as methanol, ethanol, propanol, butanol, and THF are suitable.

Following reduction, upon acidification lactonization occurs. Most organic solvents are suitable such as methylene chloride, ethyl acetate, chloroform, methanol, ethanol, butanol and various mixtures thereof. Additionally, virtually any strong organic or mineral acid is suitable, such as sulfuric acid, methane sulfonic acid, hydrochloric acid, phosphoric acid, p-TSA or hydrochloric acid. It is preferred that the acids be p-TSA. Hence, ethisterone (I) is readily transformed to the lactone (IV) upon protecting the Δ4-3-keto group as the ketal, formation of the carboxylate function directly without having to protect the 17β-hydroxy group, reduction and acidified lactonization, see Chart A.

Chart B discloses the transformation of the lactone (IV) to spironolactone (VIII).

The transformation of the lactone (IV) to the Δ4,6-lactone (VII) has been performed in a number of ways, see the discussion in the Background of the Invention. More particularly, see U.S. Pat. No. 3,452,008 for the transformation of a 19-nor lactone to the corresponding 19-nor-Δ4,6-lactone. In addition, U.S. Pat. No. 2,900,383 (Example 2) discloses the transformation of the lactone (IV) to the Δ4,6- lactone (VII). See also Organic Reactions in Steroid Chemistry, Fried and Edwards, Reinhold and Co., (1972) Vol. 1, Chapter 6, page 265–363.

In the process of the present invention the lactone (IV) is transformed to the 3-acyloxy-Δ3,5-lactone (V) by reaction with an acid anhydride or a compound of the formula $CH_3—C(CH_2)—OCOR_3$ in the presence of an acid or base catalyst. Both organic and inorganic acid catalysts may be used, for example, hydrochloric acid, sulfuric acid, p-TSA, methane sulfonic acid, phosphoric acid or hydrobromic acid. Pyridine and triethylamine are suitable base catalysts. The mixture is stirred at room temperature (20°–25°) until the reaction is complete as measured by TLC. Various solvents may be used, such as methylene chloride, THF, chloroform, or acetic anhydride. It is preferred that the solvent be acetic anhydride. The reaction is best performed under nitrogen by mixing a 30% HBr/acetic acid mixture with the lactone (IV). The temperature may be increased to shorten reaction time, however, this decreases purity somewhat. It is preferred that the esterifying agent be an anhydride and it is preferred that the anhydride be acetic anhydride where $R_3$ is methyl.

The ester (V) is halogenated to form the halo lactone (VI) by reaction with a halogenating agent in the presence of base. It is preferred that the halogenating agent be selected from the group consisting of bromine, chlorine, iodine, n-bromosuccinimide or n-chlorosuccinimide. Various bases suitable are calcium carbonate, sodium hydroxide, potassium hydroxide, sodium acetate, sodium benzoate, aniline, triethylamine, pyridine, morpholine, sodium phosphate, potassium carbonate, sodium bicarbonate or DBU. It is preferred that the base is calcium carbonate. The halo lactone (VI) may be isolated if so desired. However, it is more convenient and preferred to continue the reaction without isolation of the halo lactone (VI).

The halo lactone (VI) is converted to the Δ4,6-lactone (VII) by heating to 20°–150° in the presence of a base. It is more preferred that the reaction is heated in the temperature range of 80°–110°. The base utilized for the halogenating reaction can also be used here for the transformation of the halo lactone (VI) to the Δ4,6-lactone (VII). The reaction is usually complete in about 1 hour.

The Δ4,6-lactone (VII) is transformed to spironolactone (VIII) by methods well known to those skilled in the art, in particular see U.S. Pat. No. 3,013,012 (Example 3). The Δ4,6-lactone (VII) is heated (about 100°) with thiolacetic acid under nitrogen atmosphere until the reaction is complete (about 6 hours). While the literature indicates that this reaction can be performed neat it is more advantageous and economical to use solvents such as toluene, chloroform, THF and dioxane. The reaction proceeds very slowly at temperatures below 70° therefore, heating is necessary. Since the reaction is radical in nature initiators other than heat may be used, for example, light, chemical initiators such as dibenzoylperoxide or azobis(isobutyronitrile) with subsequent lowering of the reaction temperature. The reaction may also be catalyzed by Lewis acids, such as aluminum trichloride, titanium tetrachloride, or tin tetrachloride, in solvents such as methylene chloride, chloroform, or THF, see T. Mukaiyama et al., Chem. lett. 355 (1973).

DEFINITIONS

The definitions and explanations below are for the terms as used throughout the entire patent aplication including both the specification and claims.

All temperatures are in degrees Centigrade.
TLC refers to thin-layer chromatography.
THF refers to tetrahydrofuran.
DMF refers to dimethylformamide.
DBU refers to 1,5-diazabicyclo[5.4.0]undec-5-ene
p-TSA refers to p-toluenesulfonic acid.
NMR refers to nuclear (proton) magnetic resonance spectroscopy, chemical shifts are reported in ppm (δ) downfield from TMS.
psi refers to pounds/square inch.
A is a hydrogen atom or methyl group.
x is 0 or 1.
R is alkyl of 1 thru 5 carbon atoms, phenyl or triphenylmethyl.
Metal is lithium, sodium or potassium.
$R_3$ can be same or different and are alkyl of 1 thru 6 carbon atoms or phenyl.
$R_6$ is a chlorine, bromine or iodine atom.
When the term "alkyl of 1 thru 5 carbon atoms" is used it includes the isomers thereof when they exist.
A hydrogenating catalyst is a compound or complex which catalyzes the hydrogenation of the triple bond in the 17α side chain of a compound of formula (III) without catalyzing hydrogenation of the Δ5 double bond.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

3,3-Ethylenedioxy-17β-hydroxy-17α-ethinylandrost-5-ene (II)

Trimethylorthoformate (20 ml.) and p-TSA monohydrate (1.9 g.) is added to a slurry of ethisterone (I, 31.34 g.) in ethylene glycol (100 ml.) and methanol (200 ml.). The mixture is heated to 50° until the reaction is complete (about 5 hours) as measured by TLC. The mixture is cooled to 5° and water (200 ml.) containing sodium acetate (6.6 g.) is added. The resulting suspension is filtered to recover the solids which are dried at 50° under reduced pressure (20 mm) for 6 hours to give the title compound, m.p. 245°–250°; NMR (CDCl$_3$) 0.87, 1.03, 2.57, 3.97 and 5.23δ.

EXAMPLE 2

3,3-Ethylenedioxy-17β-hydroxy-17α-(2-carboxyethinyl)-androst-5-ene (III)

3,3-Ethylenedioxy-17β-hydroxy-17α-ethinylandrost-5-ene (II, Example 1, 8.56 g.) is added to dry THF (280 ml.) and the mixture cooled to −30°. n-Butyl lithium in hexane (1.42 M, 44 ml.) is added and the mixture is subjected to carbon dioxide pressure (20 psi). After 3 hours the solvent mixture is removed by reduced pressure to give the di-lithium salt of the title compound.

EXAMPLE 3

17α-(2-carboxyethyl)-17β-hydroxyandrost-4-en-3-one lactone (IV)

Methanol (160 ml.) is added to 3,3-ethylenedioxy-17β-hydroxy-17α-(2-carboxyethinyl)-androst-5-ene (III, Example 2). Triethylamine (8 ml.), Palladium on charcoal (5%, 0.8 g.) are added and the mixture is subjected to hydrogen (20 psi). After hydrogenation the mixture is filtered thru Celite, the filtrate is subjected to reduced pressure to remove the solvents.

THF (100 ml.) is added followed by hydrochloric acid (6 N, 50 ml.) and the mixture stirred at 20°–25° until the reaction is complete as measured by TLC. The mixture is then extracted with chloroform to obtain the steroid in solution and the chloroform removed by reduced pressure to give the title compound which upon crystallization from ethyl acetate-hexane gives m.p. 144°–146°; NMR (CDCl$_3$) 1.00, 1.23, and 5.70δ.

EXAMPLE 4

3-Acetoxy-17α-(2-carboxyethyl)-17β-hydroxyandrosta-3,5-diene lactone (V)

To 17α-(2-carboxyethyl)-17β-hydroxyandrost-4-en-3-one lactone (IV, Example 3, 10 g.) dissolved in acetic anhydride (100 ml.) under nitrogen is added a hydrogen bromide-acetic acid mixture (30%, 0.2 ml.). The mixture is stirred at 20°–25° for about 16 hours. Water (2400 ml.) is then added, the resulting suspension stirred for 2 hours, filtered and the solids dried under reduced pressure (20 mm) for 2 hours at 40° to give the title compound, m.p. 153°–164°; NMR (CDCl$_3$) 0.97, 1.0, 2.13, 5.40 and 5.7δ.

EXAMPLE 5

6-Bromo-17α-(2-carboxyethyl)-17β-hydroxyandrost-4-en-3-one lactone (VI)

Water (3 ml.) and calcium carbonate (3.0 g.) is added to DMF (100 ml.) containing 3-acetoxy-17α-(2-carboxyethyl)-17β-hydroxyandrosta-3,5-diene lactone (V, Example 4, 3.3 g.) under a nitrogen atmosphere. The mixture is cooled to −10° followed by addition of a cold (0°) solution of bromine (1.43 g.) in DMF (14 ml.) over a 10 minute period. The title compound can be isolated if desired.

EXAMPLE 6

17α-(2-carboxyethyl)-17β-hydroxyandrosta-4,6-dien-3-one lactone (VIII)

The 6-bromo-17α-(2-carboxyethyl)-17β-hydroxyandrost-4-en-3-one lactone (VI, Example 5) mixture is heated to 95° until the reaction is complete (about 1 hour) as measured by TLC. The mixture is cooled to 20°–25° and the inorganic solids are removed by filtration. Water (1000 ml.) is added to the filtrate which causes precipitation of the steroid. The solids are collected by filtration and dried under reduced pressure (20 mm) at 50° for 6 hours to give the title compound, m.p. 156°–160°; NMR (CDCl$_3$) 1.03, 1.13, 5.67 and 6.12δ.

EXAMPLE 7

Spironolactone (VIII)

Thiolacetic acid (5.3 ml.) is added to toluene (15 ml.) containing 17α-(2-carboxyethyl-17β-hydroxyandrosta-4,6-dien-3-one lactone (VIII, Example 6, 5.1 g.) under nitrogen. The mixture is heated at 100° until the reaction is complete (about 6 hours) as measured by TLC. The mixture is cooled and the solvent is removed by reduced pressure. The solid is crystallized from methanol, m.p. 136°–143°; NMR (CDCl$_3$) 1.0, 1.57, 2.33, 4.0 and 5.7δ.

I claim:

1. A process for producing spironolactone (VIII) which comprises
   (1) reacting ethisterone (I) with a glycol of the formula:

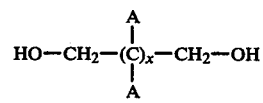

to give the hydroxy glycol (II)

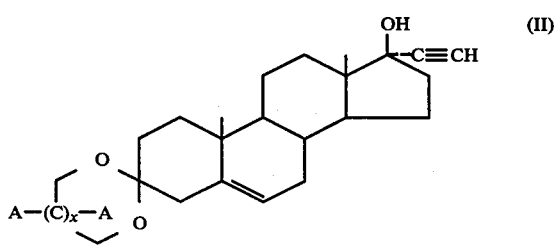

(2) carboxylating the hydroxy glycol (II) by reaction with carbon dioxide in the presence of R-Metal to give the acid glycol (III)

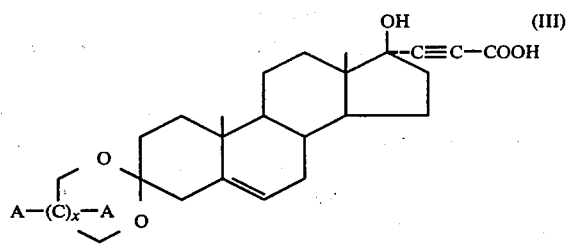

(3) reducing and cyclizing the acid glycol (III) by hydrogenation in the presence of a hydrogenating catalyst followed by acidification to give the lactone (IV)

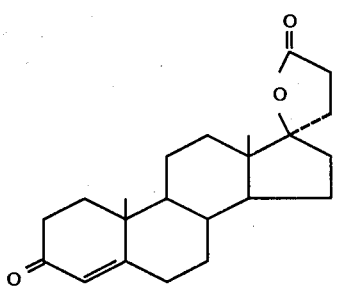

(4) esterifying the lactone (IV) by reaction with an esterifying agent selected from the group consisting of an anhydride of the formula $(R_3—CO)_2O$ or a compound of the formula $CH_3—C(CH_2)—OCOR_3$ to give the ester (V)

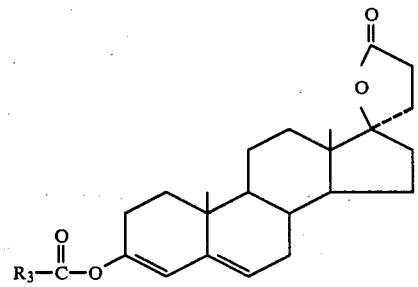

(5) halogenating the ester (V) by reaction with a halogenating agent to give the halo lactone (VI)

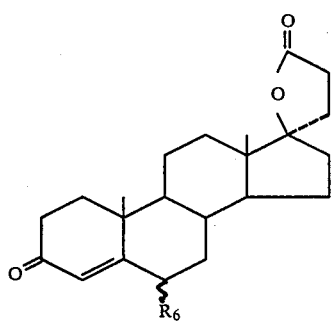

(6) heating the halo lactone (VI) in a temperature range of 20°–150° in the presence of a base to give the Δ4,6-lactone (VII)

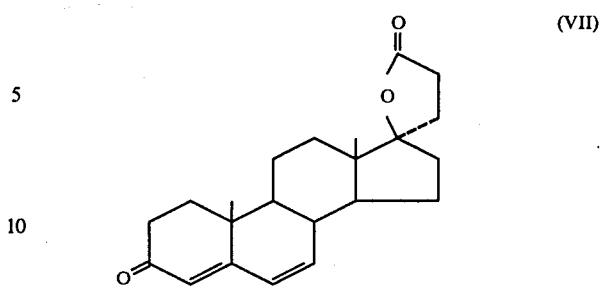

and (7) thiolacetylating with thiolacetic acid to give spironolactone (VIII) where A, x, R, Metal, $R_3$ and $R_6$ are defined in the specification.

2. A process according to claim 1 where x is 0 and the glycol is ethylene glycol.

3. A process according to claim 1 where x is 1 and A is a hydrogen atom where the glycol is propylene glycol.

4. A process according to claim 1 where R is n-butyl or phenyl.

5. A process according to claim 4 where R is n-butyl.

6. A process according to claim 1 where Metal is lithium.

7. A process according to claim 1 where the hydrogenating catalyst is selected from the group consisting of palladium on carbon, platinum on carbon, platinum dioxide, palladium on barium carbonate or palladium on calcium carbonate.

8. A process according to claim 7 where the hydrogenating catalyst is palladium on carbon.

9. A process according to claim 1 where the esterifying agent is an anhydride.

10. A process according to claim 9 where the anhydride is acetic anhydride.

11. A process according to claim 1 where the halogenating agent is selected from the group consisting of chlorine, bromine, iodine, N-bromosuccinimide or N-chlorosuccinimide.

12. A process according to claim 11 where the halogenating agent is bromine.

13. A process according to claim 1 where the halo lactone (VI) is heated in the temperature range of 80° to 120°.

14. A process according to claim 1 where the base is selected from the group consisting of calcium carbonate, sodium hydroxide, potassium hydroxide, sodium acetate, sodium benzoate, analine, triethylamine, pyridine, morpholine, sodium phosphate, potassium carbonate, sodium bicarbonate and DBU.

15. A process according to claim 14 where the base is calcium carbonate.

16. A process for producing spironolactone (VIII) which comprises (1) reacting ethisterone with ethylene glycol to give 3,3-ethylenedioxy-17β-hydroxy-17α-ethinylandrost-5-ene (II).

(2) carboxylating by reaction with carbon dioxide in the presence of n-butyllithium to give 3,3-ethylenedioxy-17β-hydroxy-17α-(2-carboxyethinyl)-androst-5-ene (III).

(3) reducing and cyclizing by hydrogenation in the presence of palladium on carbon followed by acidification with dilute hydrochloric acid to give 17α-

(2-carboxyethyl)-17β-hydroxyandrost-4-en-3-one lactone (IV)

(4) esterifying by reaction with acetic anhydride to give 3-acetoxy-17α-(2-carboxyethyl)-17β-hydroxyandrosta-3,5-diene lactone (V).

(5) halogenating by reaction with bromine to give 6-bromo-17α-(2-carboxyethyl)-17β-hydroxyandrost-4-en-3-one lactone (VI)

(6) heating to 80°–120° in the presence of calcium carbonate to give 17α-(2-carboxyethyl-17β-hydroxyandrosta-4,6-dien-3-one lactone (VII), and (7) thiolacetylating with thioacetic acid to give spironolactone (VIII).

17. A process for producing 17α-(2-carboxyethyl)-17β-hydroxyandrosta-4,6-dien-3-one lactone (VII) which comprises (1) reacting ethisterone (I) with a glycol of the formula:

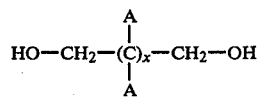

to give the hydroxy glycol (II)

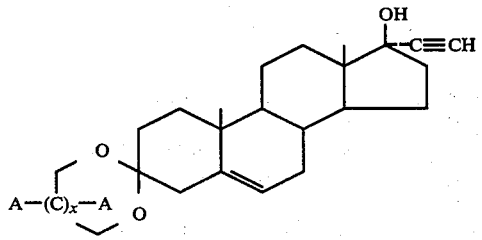

(2) carboxylating the hydroxy glycol (II) by reaction with carbon dioxide in the presence of R-Metal to give the acid glycol (III)

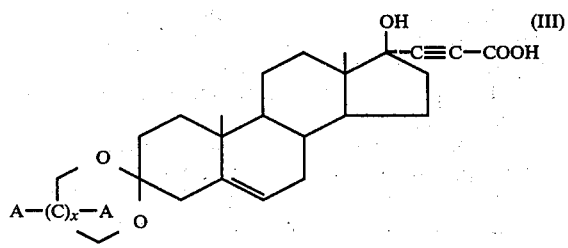

(3) reducing and cyclizing the acid glycol (III) by hydrogenation in the presence of a hydrogenating catalyst followed by acidification to give the lactone (IV)

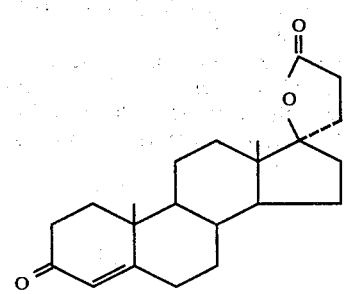

(4) esterifying the lactone (IV) by reaction with an esterifying agent selected from the group consisting of an anhydride of the formula $(R_3—CO)_2O$ or a compound of the formula $CH_3—C(CH_2)—OCOR_3$ to give the ester (V)

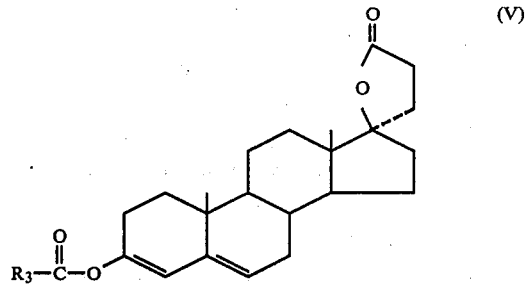

(5) halogenating the ester (V) by reaction with a halogenating agent to give the halo lactone (VI)

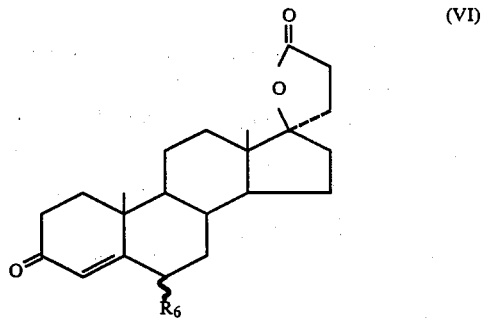

and (6) heating the halo lactone (VI) in the temperature range of 20°–150° in the presence of a base to give the Δ4,6-lactone (VII)

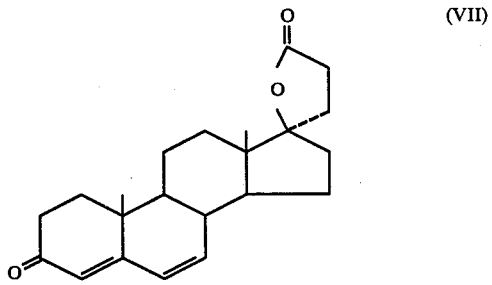

where A, x, R, Metal, $R_3$ and $R_6$ are defined in the specification.

18. A process according to claim 17 where x is 0 and the glycol is ethylene glycol.

19. A process according to claim 17 where x is 1 and A is a hydrogen atom where the glycol is propylene glycol.

20. A process according to claim 17 where R is n-butyl or phenyl.

21. A process according to claim 20 where R is n-butyl.

22. A process according to claim 17 where Metal is lithium.

23. A process according to claim 17 where the hydrogenating catalyst is selected from the group consisting of palladium on carbon, platinum on carbon, platinum dioxide, palladium on barium carbonate or palladium on calcium carbonate.

24. A process according to claim 23 where the hydrogenating catalyst is palladium on carbon.

25. A process according to claim 17 where the esterifying agent is an anhydride.

26. A process according to claim 25 where the anhydride is acetic anhydride.

27. A process according to claim 17 where the halogenating agent is selected from the group consisting of chlorine, bromine, iodine, N-bromosuccinimide or N-chlorosuccinimide.

28. A process according to claim 27 where the halogenating agent is bromine.

29. A process according to claim 17 where the halo lactone (VI) is heated in the temperature range of 80° to 120°.

30. A process according to claim 17 where the base is selected from the group consisting of calcium carbonate, sodium hydroxide, potassium hydroxide, sodium acetate, sodium benzoate, aniline, triethylamine, pyridine, morpholine, sodium phosphate, potassium carbonate, sodium bicarbonate, DBU.

31. A process according to claim 30 where the base is calcium carbonate.

32. A process for producing 17α-(2-carboxyethyl)-17β-hydroxyandrost-4-en-3-one lactone (IV) which comprises (1) reacting ethisterone (I) with a glycol of the formula:

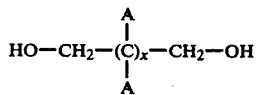

to give the hydroxy glycol (II)

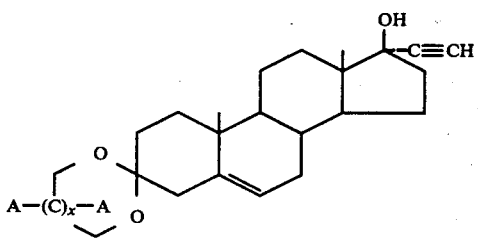

(2) carboxylating the hydroxy glycol (II) by reaction with carbon dioxide in the presence of R-Metal to give the acid glycol (III)

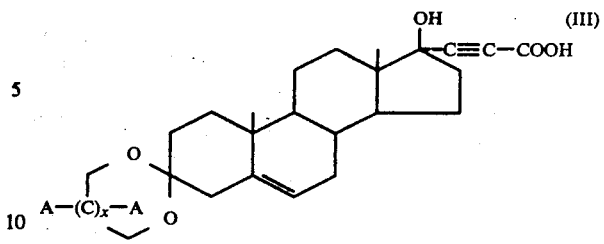

and (3) reducing and cyclizing the acid glycol (III) by hydrogenation in the presence of a hydrogenating catalyst followed by acidification to give the lactone (IV)

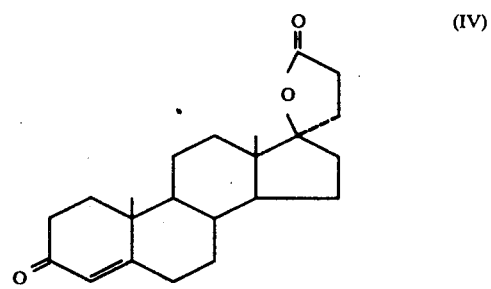

33. A process according to claim 32 where x is 0 and the glycol is ethylene glycol.

34. A process according to claim 32 where x is 1 and A is a hydrogen atom where the glycol is propylene glycol.

35. A process according to claim 32 where R is n-butyl or phenyl.

36. A process according to claim 35 where R is n-butyl.

37. A process according to claim 32 where Metal is lithium.

38. A process according to claim 32 where the hydrogenating catalyst is selected from the group consisting of palladium on carbon, platinum on carbon, platinum dioxide, palladium on barium carbonate or palladium on calcium carbonate.

39. A process according to claim 38 where the hydrogenating catalyst is palladium on carbon.

40. A process for producing 17α-(2-carboxyethyl)-17β-hydroxyandrost-4-en-3-one lactone (IV) which comprises (1) reacting ethisterone with ethylene glycol to give 3,3-ethylenedioxy-17β-hydroxy-17α-ethinylandrost-5-ene (II)

(2) carboxylating by reaction with carbon dioxide in the presence of n-butyllithium to give 3,3-ethylenedioxy-17β-hydroxy-17α-(2-carboxyethinyl)-androst-5-ene (III)

(3) reducing and cyclizing by hydrogenation in the presence of palladium on carbon followed by acidification with dilute hydrochloric acid to give 17α-(2-carboxyethyl)-17β-hydroxyandrost-4-en-3-one lactone (IV).

* * * * *